United States Patent [19]

Nordenström et al.

[11] Patent Number: 4,572,214
[45] Date of Patent: Feb. 25, 1986

[54] ELECTRODE DEVICE

[75] Inventors: Bjorn E. W. Nordenström, Rönninge; Mats J. Olsson, Tyresö, both of Sweden

[73] Assignee: URSUS Konsult AB, Stockholm, Sweden

[21] Appl. No.: 328,581

[22] PCT Filed: Apr. 10, 1981

[86] PCT No.: PCT/SE81/00112
§ 371 Date: Dec. 2, 1981
§ 102(e) Date: Dec. 2, 1981

[87] PCT Pub. No.: WO81/02839
PCT Pub. Date: Oct. 15, 1981

[30] Foreign Application Priority Data

Apr. 11, 1980 [SE] Sweden .................... 8002772

[51] Int. Cl.$^4$ .............................................. A61N 1/04
[52] U.S. Cl. .................................................... 128/785
[58] Field of Search ............... 128/303.13, 303.15, 128/303.17, 303.18, 784-786; 604/21

[56] References Cited

U.S. PATENT DOCUMENTS

| 452,220 | 5/1891 | Gunning | 128/786 |
| 3,411,507 | 11/1968 | Wingrove | 128/784 X |
| 3,769,984 | 11/1973 | Muench | 128/786 |
| 3,952,742 | 4/1976 | Taylor | 128/785 X |
| 4,103,690 | 8/1978 | Harris et al. | 128/785 |

FOREIGN PATENT DOCUMENTS

| 1007960 | 5/1957 | Fed. Rep. of Germany | 128/303.17 |
| 2324658 | 12/1974 | Fed. Rep. of Germany | 128/303.17 |

Primary Examiner—Lee S. Cohen
Attorney, Agent, or Firm—Frishauf, Holtz, Goodman & Woodward

[57] ABSTRACT

An electrode device for treatment of biological tissue comprising an electrode unit (1, 3, 3') and a supply unit (4) electrically insulated against the surrounds for supply of electricity from a voltage source to the said electrode unit (1, 3, 3'). The supply unit (4) is designed pliable and contains at least one duct for one or a plurality of electrical conductors (5-7) and for transport and guidance of aids (12-15, etc.) to and from the electrode unit (1, 3, 3').

13 Claims, 6 Drawing Figures

ELECTRODE DEVICE

This invention relates to an electrode device intended to be temporarily inserted into the body of a living being and essentially locally to treat biological body tissue therein and subsequently, upon completion of the treatment, to be removed. The device includes an electrode unit introducable into the body tissue which it is intended to treat, and a supply unit electrically insulated against other parts of the body for the supply of electricity from a voltage source to the electrode unit.

Various electrodes are already known, for example through the U.S. Pat. Nos. 4,103,690 and 3,348,548 and through the German Pat. Nos. 577 722, 651,428 and 1 143 937.

Known electrode designs for the treatment of biological tissue are unsuitable for several reasons.

In order, for example, to treat a tumour with direct current, the electrode which is to be inserted in the tumour and which is arranged to electrically interact with a secondary electrode which is located outside the tumour must be localized with great precision in the centre of the tumour. With prior art electrodes, it is very difficult to achieve exact positioning and retention of the electrode in the tumour. One of the reasons for this is that the tissue and the tumour may move, for instance as a consequence of the respiratory motions of the patient. Moreover, the tumour, where the point of the electrode reaches to and is to be inserted into the tumour, may slide aside in surrounding softer tissue. This means that repeated attempts frequently have to be made in order for an acceptable positioning of the tumour to be obtained.

Severe problems in the treatment of tissues also arise as a consequence of gas formation, dehydration and/or material deposition on the surfaces of the electrode.

One of the objects of the present invention is to provide an electrode device which permits certain and exact insertion and retention as well as removal of the active electrode unit in a biological tissue without being moved out of position, for example in a tumour. A further object of the invention is to provide an electrode device with the aid of which gases generated at the surfaces of the electrode can be sucked out and liquid and/or medication can be supplied to the tumour.

These and other objects are obtained with the electrode device according to the present invention, in that said device includes generally cylindrical hollow electrode means to be introduced into body tissue to reach a treatment point in relation to the body tissue for applying a potential at the treatment point. A tubular pliable supply unit provides for a supply of electricity from a voltage source to the electrode means, one end of the supply unit being coaxially fitted to the electrode means and the other end of the supply unit being arranged to extend outside the body. The supply unit has at least one duct extending over its length and communicating at one end with the outside of the body, and at the other end with an end of the electrode means which opens towards the treatment point in the body tissue. Means operatively associated with the electrode means introduces the electrode means into the body tissue, and means are provided for anchoring the electrode means at the treatment point in relation to the body tissue to be treated.

Other essential features of the present invention are evident from the accompanying claims. One embodiment of the invention is described below and with reference to the accompanying drawings, wherein

Figure 1:
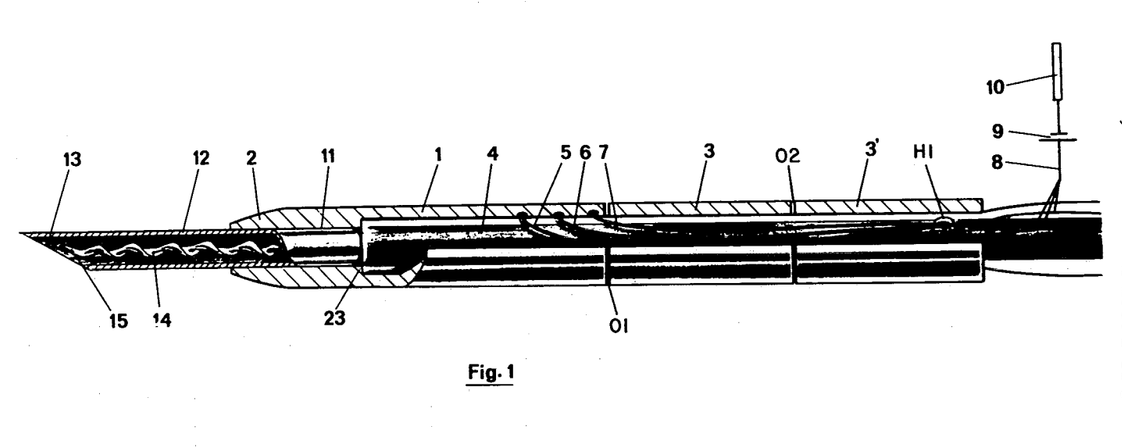
FIG. 1 shows a cut-away view of an example of an embodiment of the electrode device according to the invention.

The embodiment of the electrode device shown in FIG. 1 comprises an electrode unit, manufactured for example of platinum and having a front section 1 with a pointed or narrowing cylindrical end 2 and one or more axially spaced rear cylindrical rings 3, 3' defining annular openings $O_1$ and $O_2$. These parts have a diameter of approx. 1.9 mm. The electrode unit is shown here to consist of three parts to illustrate that electrode units with different axial lengths for tissue areas of different sizes can be built up from a standardized front section 1 and auxiliary rings 3, 3' since a large electrode surface is required in order to enable sufficiently large current intensities to pass through the tissue area to be treated within reasonable time.

The front section 1 of the electrode unit, which obviously can be used without auxiliary rings 3, 3', if for example a cancer tumour which is to be treated is of such a size that the length of the part 1 is sufficient, is attached by pressure to one end section of a supply unit 4 which in this case consists of a tube 4. This tube 4 is made pliable in order to be able to accompany movements in tissues and may be made for example of the plastic marketed under the trade mark Teflon. The rear rings 3 and 3' respectively are similarly attached by pressure to the tube 4. Attached to the inside of the cylindrical electrode section 1 are one or more electrical conductors 5, 6, 7, which are for example brazed or soldered. In the shown example, the conductors are three in number. The conductors 5–7 which in the same way as the electrode rings 1, 3, 3' are bright (blank) and thus uninsulated in the shown embodiment, are clamped between the cylindrical inner surfaces of the parts 3, 3' and the cylindrical jacket surface of the tube 4. By this means, good electrical contact is afforded between the electrical conductors 5–7 and the rings 3, 3'. The three conductors 5–7 are inserted into the interior of the tube 4 through a hole H1 sited within the region for the ring 3', and are introduced via the interior of the tube 4 to, for example, one terminal 8, in the shown embodiment the positive terminal, of a direct voltage source 9. The second terminal of the latter is in this case connected to a second electrode 10 which is located at a suitable distance from the tube in a conductive medium in the body.

We have thus been able to show that the walls of the blood vessels function as insulators around a conductive medium—the blood plasma. Since a tumour is supplied by the surrounding blood vessels, a closed electrical circuit is obtained by this means, with the blood vessels acting as mutually parallel electric conductors. Other conductive media in the body may nevertheless be used, for example tissue fluid, brain fluid, gall fluid, urine, gland secretion, etc.

When an electrode which is inserted in a tumour acts as a positive electrode, a powerful emission of protons is obtained upon decomposition of water, resulting in the tissue becoming highly acidic and in destruction of the tumour close to the electrode. Tumour cells possess negative surplus charges and are therefore retained by the positive electrode. At the same time, gas—for example chlorine gas and oxygen gas—is generated at the positive electrode and the gases deposit themselves on the surface of the electrode, thus impeding the process. Further biological effects in the electrical field have been revealed and consist of electro-osmosis, electroforetic transports, accumulation of white blood corpuscles around the anode and extended formation of blood clots in the capillaries around the anode, all factors contributing to the treatment.

If medications such as cytostatics or antibiotics are desired in a high local concentration within a treatment area, such medications can be attracted towards the electrical field of an electrode if the medication is imparted an electrical polarity which permits its electroforetic attraction towards the electrode concerned. In this case, the medication can be administered in supply ducts, such as blood paths, gland paths, etc. By means of the present invention, the medication can also be administered via the electrode duct. If the same polarity is given to the electrode as to the medication, this is repelled in the tissue. If the opposite polarity is applied, the medication is retained in the vicinity of the electrode.

The tube 4 has an inner cylindrical duct which is substantially equally as large as the cylindrical duct 11 in the front section of the electrode unit 1. By giving a lug 23 for the end of the tube 4, a slightly greater extent in the direction towards the centre than that corresponding to the wall thickness of the tube 4 in itself, an additional lug is obtained against which a cylindrical body or ball (not shown) connected with a stiff but pliable thin wire can be inserted in the tube 4 and act as a seal to close the opening in the end of the electrode unit 1 if necessary. A cannula with a diameter of approx. 1 mm may be introduced through the tube 4 and through this duct 11. The said cannula is provided with, for example, an obliquely ground off tip 13. The cannula 12 can be inserted into the position shown in FIG. 1, i.e. to a position beyond the end 2 of the electrode unit 1 and after insertion in the tissue together with the electrode unit will form a guide device for the electrode unit 1, 3. While the cannula 12 is being inserted in a tumour, it is possibly rotated around its longitudinal axis. A wireshaped anchoring device 14, 16, which in the embodiment example has a screw-shaped end section 14 which is terminated with a sharp point 15 is introducable into the cannula 12. The end of the anchoring device may instead be provided with other suitable means for improving the anchoring in and increasing the contact area against the tumour, for instance with hooks or barbs.

Figure 1A:
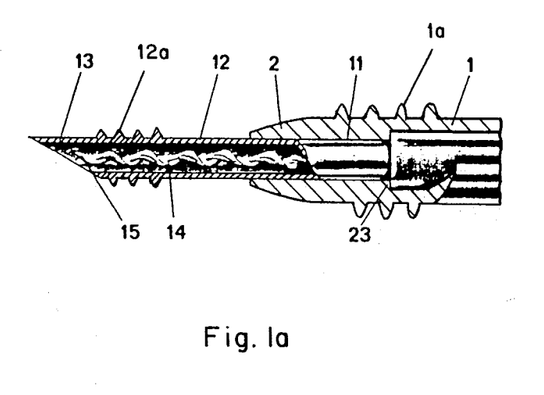
FIG. 1a shows a modification of the embodiment of FIG. 1.

As an alternative or a compliment, the shell surface of the cannula 12 and/or the electrode unit 1 may be screw-shaped 12a, 1a (see FIG. 1a) to facilitate introduction into and increase the contact surface against the tumour.

Figure 2:
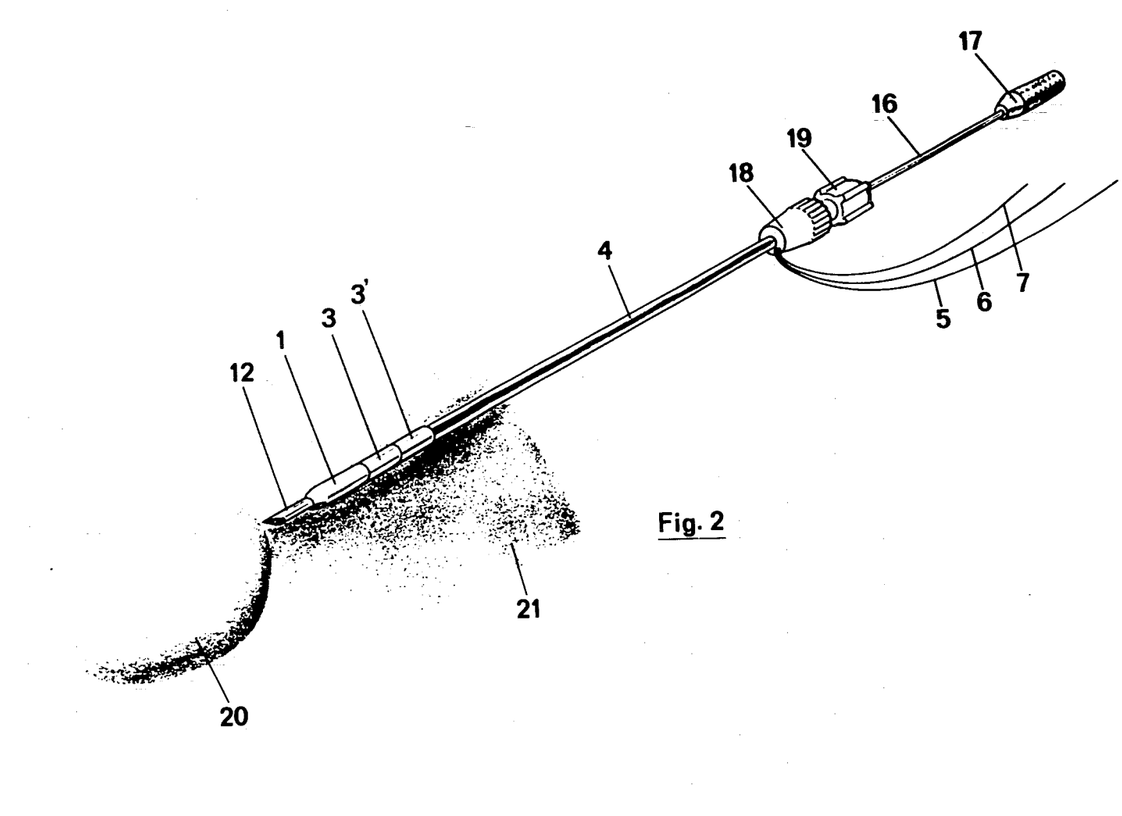
FIG. 2 shows a first stage in the introduction of the electrode device in the direction towards a tumour.
Figure 3:
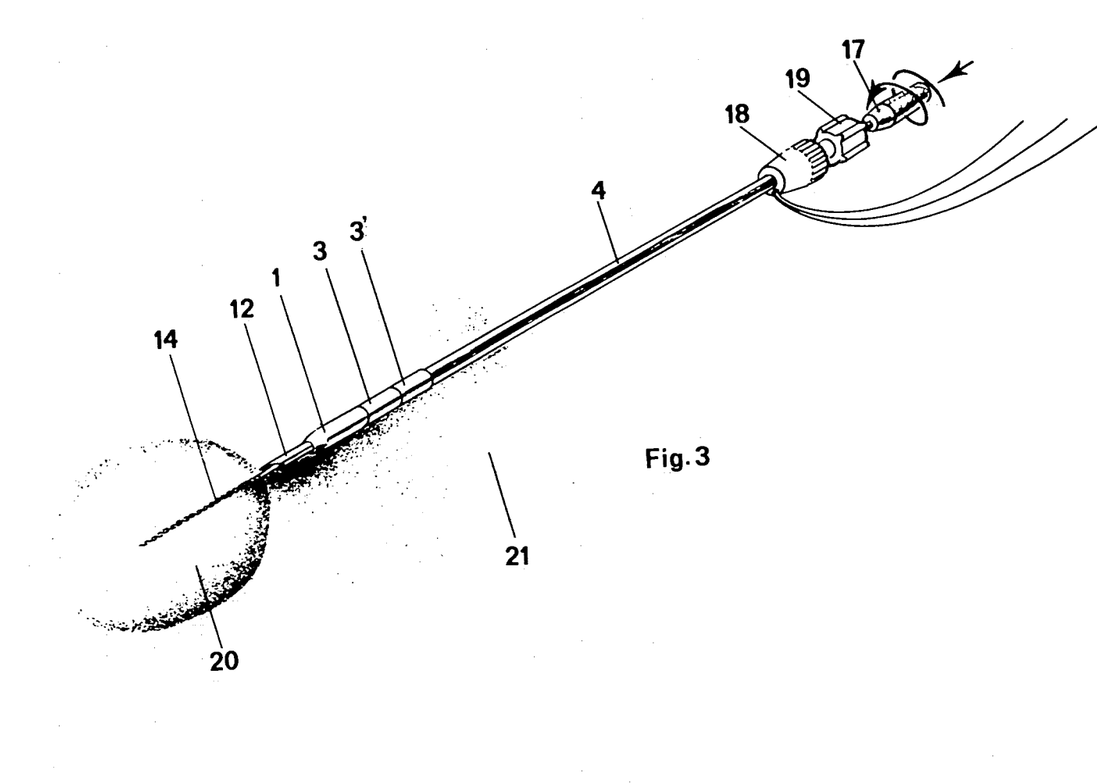
FIG. 3 shows the introduction of an aid, for example an anchoring device, in the tumour.
Figure 4:
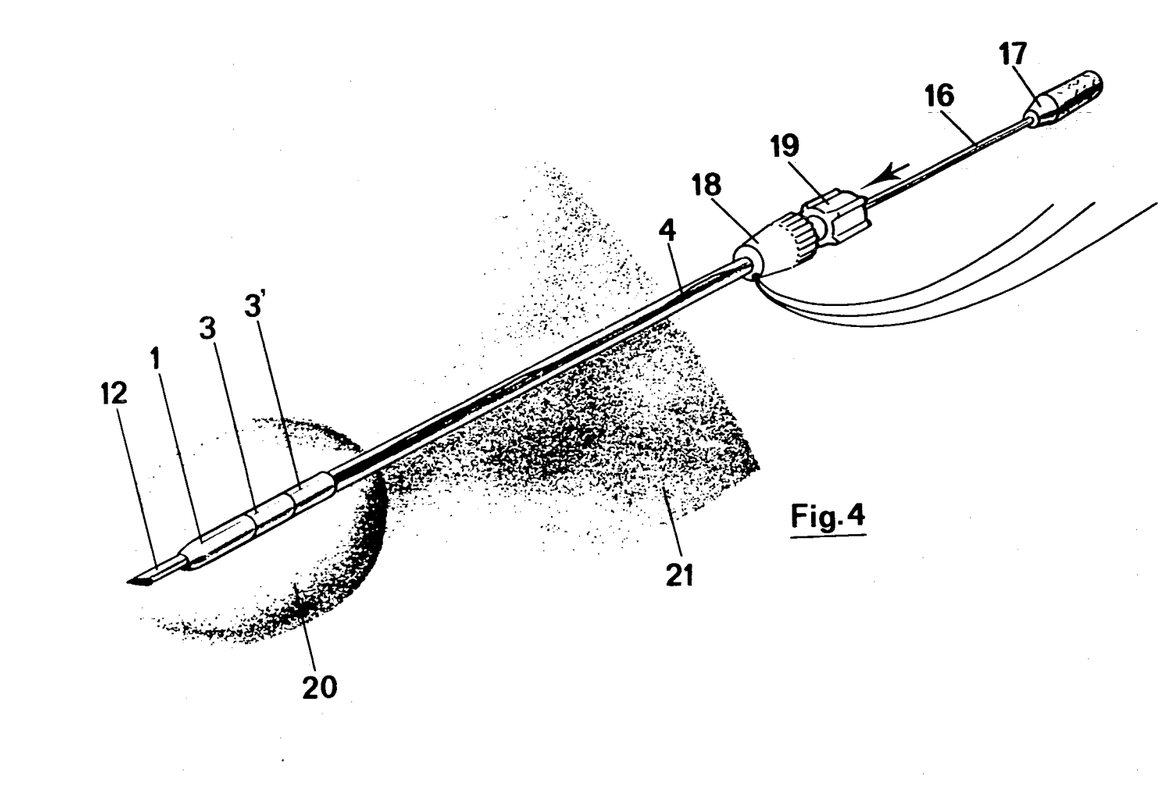
FIG. 4 shows the electrode device inserted with the aid of the anchoring device and a stiffening member, for example a cannula.

The anchoring device, designated by reference numeral 16 in FIGS. 2 and 4, extends throughout the entire cannula 12 and some way beyond the end of the cannula facing away from the tip 13 and is provided with a knob 17 by means of which the screw-shaped end section 14 can be rotated. The electrical conductors 5–7 emanate through a connector 18, for example in the form of a screw socket. In this position of the cannula socket 19—see FIG. 2—the cannula 12 is entirely inserted in the tube 4 and in the electrode unit 1 and protrudes beyond the electrode unit 1.

FIGS. 2–5 illustrate various stages in application of the electrode unit into a tumour 20 which is surrounded by body tissue 21.

FIG. 2 shows how the electrode device has been passed through the body tissue 21 as far as the tumour 20 and the cannula 12 is here in its fully inserted position, whereupon the cannula socket 19 rests against the screw socket 18. When the tip of the cannula 12 has reached as far as the tumour 20, the anchoring device 16 will be in such a position that its screw-shaped end 14 lies entirely retracted in the cannula 12.

In the next stage, the anchoring device 16 is anchored by means of its tip 14, which may, for example, be screw-shaped, in the tumour 20. For this purpose, the tube 4 and the cannula 12 are retained in the position shown in FIG. 2 and the knob 17—see FIG. 3—is turned in the entry direction of the screw-shaped tip 14 under light axial pressure. The tip 15 of the screw 14 first reaches the occasionally relatively hard tumour tissue and easily penetrates the surface of the tumour without essentially disturbing the position of the tumour 20. As the knob 17 continues to be turned, the screw 14 is drilled into the tumour 20, forming a reliable anchorage for the entire electrode device—see FIG. 3. When the screw has reached its intended position in the tumour 20—something which in certain cases may require repeated attempts—and which position may, for example, be checked by X-ray fluoroscopy, the cannula socket 19 is passed inwards in the direction towards the tumour 20, whereby the cannula 12 and the electrode section 1 are moved in over the screw 14 and leave tumour cells in the threads of the latter—see FIG. 4. In this position, the anchoring device 16 serves as a guiding device for the cannula 12 and thus for the electrode unit, the cannula 12 also being rotatable during the movement in order to facilitate insertion. The electrode unit 1, 3, 3' is moved into the tumour 20 together with the cannula 12 and the cannula 12 serves during this movement as a support for the pliable supply unit 4 (the tube) and when the electrode unit 1, 3, 3' attached to the tube 4 reaches the intended position in the tumour 20, both the cannula 12 and the anchoring device 16 are withdrawn from the front section 1 of the electrode and out of the tube 4 with accompanying tumour material, which may be used to advantage for cytological check.

The anchoring device 16—either threaded or unthreaded—may in certain cases be used as a temporary electrode for local destruction of tissue around the anchoring device 16. In this case, the device is for example provided with a thin coating of electrical insulation, for example the plastic marketed under the trade mark Teflon, with the exception of the portion which is intended to be inserted into the tumour. The anchoring device is then connected either to a suitably sited electrode for direct current treatment or to a large plate electrode applied to the surface of the body for application of high frequency alternating current. When heat develops around the non-isolated part of the anchoring device in the tumour, local tissue destruction is accomplished which has a therapeutic effect and gives a lengthwise extending tissue cavity, into which, for example, the cannula 12 and the electrode unit 1, 3, 3' can thus be more easily inserted.

Figure 5:
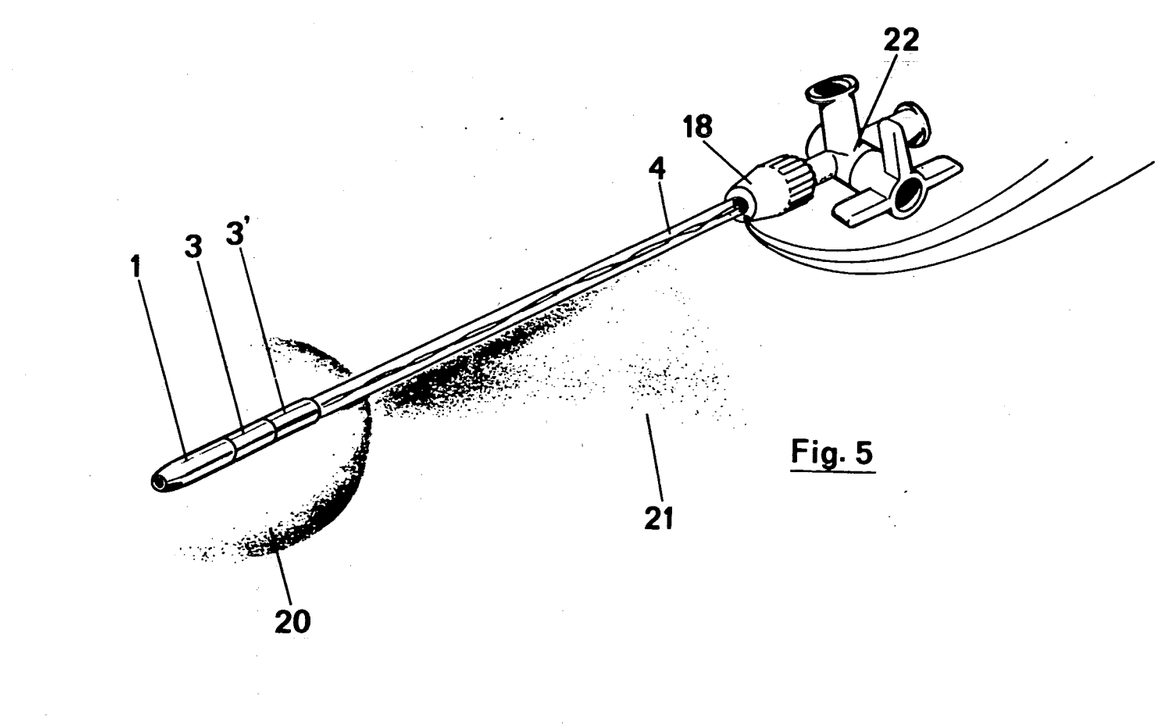
FIG. 5 shows the electrode device with the anchoring device and cannula removed. According to FIG. 5, the electrode device is in the treatment position in the tumour and a three-way cock is connected to the supply unit for extraction of gas and/or introduction of liquid or medication.

At this juncture, a cock 22 can now be inserted, as shown in FIG. 5, to the connector unit or the screw socket 18 in order to make possible, for example, the introduction of fluids or medication to the tumour 20 through the free duct in the tube 4 via perforations or holes (not shown) in this tube under the electrode units 1, 3, 3' and in or between the walls of the electrodes 1, 3, 3' and/or for removal of gas or fluid from the tumour 20. For example, physiological sodium chloride solution may be introduced in order to increase the conductivity of the tumour 20 around the electrode unit. It is also possible for example to introduce cell poison.

The cannula 12, which for example is made of stainless steel, should have a good fit against the electrode unit 1 and against the inside of the tube 4 but must slide easily in order to be insertable into and removable from the electrode unit 1 and the tube 4 without any greater effort. The anchoring device 16, which for example is made of stainless steel, has a good fit in the cannula 12.

The above described anchoring device 16 is made of rigid metal wire but it is also possible to use a flexible material, for instance spirally wound metal wire.

Through the elaboration of the electrode device, a structure is obtained which is soft, pliable and flexible and thus able to accompany tissue movements, for instance muscle movements, respiratory movements, etc. and can be introduced, for example, into a curved gall passage without being broken.

In the drawings, the electrical conductors 5-7 are shown to run inside the tube 4 but they may obviously instead be embedded in the wall of the tube 4.

The invention is primarily intended for treatment of cancer tumours in the human body but is naturally also usable in animal bodies and may similarly be used to treat other disease conditions in tissues.

We claim:

1. An electrode device arranged to be temporarily introduced into the body of a living being and essentially locally for treating biological body tissue, and to be subsequently removed from the body upon completion of the treatment, comprising:
   generally cylindrical hollow electrode means arranged to be introduced into generally solid body tissue to reach a certain treatment point in relation to the body tissue for applying an electric potential at said treatment point, wherein one end of said electrode means has an opening which is adapted to be open toward the treatment point;
   a tubular pliable supply unit for providing a supply of electricity from a voltage source to said electrode means, wherein one end portion of said supply unit is coaxially fitted to said electrode means, and another, opposite end portion of said supply unit is arranged to extend outside the body, said supply unit being insulated electrically against other body parts not to be treated;
   wherein said supply unit has at least one duct extending over the length thereof to communicate at one end with the outside of the body, and to communicate at the other end with the opening in said one end of said electrode means which opening is adapted to be open toward the treatment point in the body tissue, said duct providing a fluid passage in said supply unit which is in open fluid communication between said treatment point in the body tissue and a position outside the body, and which passage is closed in relation to said other body parts not to be treated;
   at least one electrical conductor contained in said duct in said supply unit and electrically connected to said electrode means for excitation of said electrode means wherein said electrical conductor is insulated electrically from said other body parts by a wall of said supply unit;
   means operatively associated with said electrode means for introducing said electrode means into the body tissue, and
   means for anchoring said electrode means at said treatment point.

2. The electrode device according to claim 1, wherein said electrode means is formed so that an end portion which includes said one end of said electrode means which opens toward said treatment point has an increasingly narrow outer circumference in the direction toward said one end.

3. The electrode device according to claim 1, wherein said one end portion of said tubular supply unit is surrounded coaxially by said electrode means, and the portion of the wall of said supply unit which is surrounded by said electrode means has at least one wall opening therein, said at least one electrical conductor being passable through said wall opening to the interior of said supply unit.

4. The electrode device according to claim 3, wherein said at least one electrical conductor passes through said at least one wall opening in said supply unit to contact with said electrode means.

5. The electrode device according to claim 4, including a number of hollow cylindrical electrode units forming said electrode means and successively coaxially arranged on said supply unit, and wherein said at least one wall opening in said supply unit for said at least one electrical conductor is located at such a distance from the end of said supply unit surrounded by said electrode units so that said at least one electrical conductor can electrically contact said electrode units.

6. The electrode device according to claim 5, including a cannula which forms at least a part of said introducing means, and wherein the aggregate length of said pliable supply unit, said electrode means, and said fluid passage of said duct are adapted in relation to the length and outside dimensions of said cannula so that said cannula is insertable into said fluid passage to protude at one end beyond the portion of said electrode means located furthest from said supply unit, and so that said cannula can then be inserted into the biological body tissue into which said electrode means is to be inserted and moved relative to said electrode means from a point at the end of said supply unit outside the body.

7. The electrode device according to claim 6, wherein said cannula forms at least a part of said anchoring means.

8. The electrode device according to claim 6, including an elongate wire-like member arranged to be movable in said cannula and which device forms part of said anchoring means.

9. The electrode device according to claim 6, wherein at least one of said electrode means, said cannula and said anchoring means, is screw shaped on a portion thereof to be inserted into the biological body tissue to provide increased contact surface.

10. The electrode device according to claim 5, wherein said electrode units are mutually spaced apart to provide fluid communication between the outer surfaces of said electrode units and said supply unit.

11. The electrode device according to claim 1, including a connector at said opposite end portion of said supply unit and electrically connected to said electrical conductor.

12. The electrode device according to claim 1, wherein said electrode means is provided with an inner stop lug on the inner circumference thereof and contacting said one end portion of said supply unit.

13. The electrode device according to claim 12, wherein said one end portion of the supply unit is arranged to be located by said stop lug in the interior of said electrode means and wherein said stop lug extends radially inward toward the center of said electrode means by an amount which exceeds the wall thickness of said supply unit in the same direction, so that an additional stop is provided against which a ball or cylinder actuable with a wire can be made to rest to seal said duct at said one end portion of said supply unit.

* * * * *